United States Patent
Youngs et al.

(10) Patent No.: US 6,919,448 B2
(45) Date of Patent: Jul. 19, 2005

(54) CARBENE PORPHYRINS AND CARBENE PORPHYRINOIDS, METHODS OF PREPARATION AND USES THEREOF

(75) Inventors: Wiley J. Youngs, Akron, OH (US); Claire A. Tessier, Akron, OH (US); William G. Kofron, Akron, OH (US); Richard S. Simons, Akron, OH (US); Jered C. Garrison, Akron, OH (US)

(73) Assignee: The University of Akron, Akron, OH (US)

( * ) Notice: Subject to any disclaimer, the term of this patent is extended or adjusted under 35 U.S.C. 154(b) by 17 days.

(21) Appl. No.: 10/416,149

(22) PCT Filed: Nov. 9, 2001

(86) PCT No.: PCT/US01/50754

§ 371 (c)(1), (2), (4) Date: Nov. 28, 2003

(87) PCT Pub. No.: WO02/38566

PCT Pub. Date: May 16, 2002

(65) Prior Publication Data

US 2004/0097723 A1 May 20, 2004

Related U.S. Application Data

(60) Provisional application No. 60/247,326, filed on Nov. 10, 2000.

(51) Int. Cl.[7] ............................................ C07D 487/22
(52) U.S. Cl. ....................... 540/145; 514/410
(58) Field of Search ................................ 540/145, 410; 534/15; 514/410

(56) References Cited

U.S. PATENT DOCUMENTS

| | | | |
|---|---|---|---|
| 5,262,532 A | 11/1993 | Tweedle et al. | |
| 5,405,957 A | 4/1995 | Tang et al. | |
| 6,025,496 A | 2/2000 | Herrmann et al. | |

OTHER PUBLICATIONS

Arduengo, Anthony J., III et al, "Electronic Stabilization of Nucleophilic Carbenes." *J. Am. Chem. Soc.*, vol. 114, pp. 5530–5534 (1992).

Arduengo, Anthony J., III et al. "Homoleptic Carbene–Silver (I) and Carbene–Copper(I) Complexes." *Organometallics*, vol. 12, pp. 3405–3409. (1993).

Arduengo, Anthony J., III et al. "Imidazolylidenes, Imidazolinylidenes and Imidazolidines." *Tetrahedron*, vol. 55, pp. 14523–14534 (1999).

Garrison, Jered C. et al. "Synthesis and Structural Characterization of a Silver Complex of a Mixed–Donor N–Heterocyclic Carbene Linked Cyclophane." *Chem. Commun.*, pp. 1780–1781 (2001).

*Primary Examiner*—James O. Wilson
*Assistant Examiner*—Jason H. Johnsen
(74) *Attorney, Agent, or Firm*—Roetzel & Andress LLC

(57) ABSTRACT

The present invention includes novel N-heterocyclic carbene substituted porphyrins and porphyrinoids. The invention also includes complexes of metals and N-heterocyclic carbene substituted porphyrins and porphyrinoids. The invention further includes N-heterocyclic carbene substituted porphyrins and porphyrinoids, and metal complexes of N-heterocyclic carbene substituted porphyrins and porphyrinoids that also includes a targeting moiety or group. The compositions of the present invention are useful in the fields of diagnosis and treatment of many medical ailments.

97 Claims, No Drawings

CARBENE PORPHYRINS AND CARBENE PORPHYRINOIDS, METHODS OF PREPARATION AND USES THEREOF

CROSS REFERENCE TO RELATED APPLICATIONS

This application is the National Stage of International Application No. PCT/US01/50754, filed Nov. 9, 2001, which claims the benefit of U.S. Provisional Application No. 60/247,326, filed Nov. 10, 2000.

TECHNICAL FIELD OF THE INVENTION

The present invention relates to novel compositions of matter. The present invention more particularly relates to ligands, complexes of the ligands with metals to form ligand-metal complexes, processes for preparation of the ligands and ligand-metal complexes and uses thereof.

BACKGROUND OF THE INVENTION

Porphyrins and related tetrapyrrolic macrocycles have application in various medical procedures for the diagnosis and treatment of disease.

Magnetic Resonance Imaging (MRI) is a process in which a particular object to be viewed is exposed to a radio frequency while in the presence of a varying magnetic field. In general, MRI utilizes contrast agents to produce cross-sectional images for medical diagnosis. The use of contrast agents allows one to differentiate the target tissue of interest from the surrounding tissue in the image. The use of contrast agents with MRI, however, suffers from several limitations. For example, one major limitation of the use of certain contrast agents is the disassociation of the metal from the metal complex of the contrast agent, which can leave toxic levels of metals within the body of an patient.

Positron Emission Tomography (PET) is a type of tomography produced by the detection of gamma rays emitted from tissues after the administrations of a natural biochemical substance into which positron-emitting isotopes have been incorporated. A major limitation of the use of certain contrast agents with PET is the disassociation of the radioactive isotopes from the agent, which can leave toxic levels of radioactive elements within the body of an patient.

Porphyrins and related tetrapyrrolic macrocycles also have application in the field of Photodynamic Therapy (PDT). PDT is a technique that utilizes photosensitive compounds that have a selective affinity for diseased tissue and which accumulate in diseased tissue to a greater extent than in normal tissue. PDT involves the localization of a photosensitizing agent in or near a diseased target tissue within the body. The photosensitive compound, upon illumination and in the presence of oxygen, produces cytotoxic species of oxygen such as singlet oxygen or oxygen radicals, which destroy the diseased target tissue. The PDT technique provides a greater degree of selectivity or specificity not currently achievable with current methods of chemotherapy.

Heterocyclic carbenes have been found to be useful as complexing ligands for a wide variety of metals to produce corresponding ligand-metal complexes having good thermal and chemical stability.

The synthesis of transition metal complexes of imidazol-2-ylidenes, also known as N-heterocyclic carbenes, was first pioneered by Ofele and Wanzlick in 1968 and is a very active area of research today. The synthesis of free isolable N-heterocyclic carbenes and their complexation with transition metals was first reported by Arduengo in 1991. It is not always convenient, however, to synthesize complexes from free carbenes and transition metals. A recent advance is the use of silver bis(carbene) complexes as carbene transfer reagents.

A process for the preparation of heterocyclic carbenes is described in U.S. Pat. No. 6,025,496 to Hermann et al.

Therefore, the needs exists in the art to develop improved ligands and ligand-metal complexes for diagnostic and therapeutic applications.

SUMMARY OF THE INVENTION

The present invention, in one embodiment, provides a composition of matter comprising a N-heterocyclic carbene substituted porphyrins.

The present invention, in another embodiment, provides a composition of matter comprising a N-heterocyclic carbene substituted porphyrinoids.

The present invention, in another embodiment, further provides a complex comprising a N-heterocyclic carbene substituted porphyrin ligand and a metal bonded to said ligand.

The present invention, in another embodiment, further provides a complex comprising a N-heterocyclic carbene substituted porphyrinoid ligand and a metal bonded to said ligand.

The present invention, in another embodiment, further provides a method for preparing N-heterocyclic carbene substituted porphyrins.

The present invention, in another embodiment, further provides a method for preparing N-heterocyclic carbene substituted porphyrinoids.

The present invention, in another embodiment, further includes a method for providing a complex comprising a N-heterocyclic carbene substituted porphyrin ligand and a metal bonded to said ligand.

The present invention, in another embodiment, further provides a method for preparing a complex comprising a N-heterocyclic carbene substituted porphyrinoid ligand and a metal bonded to said ligand.

DETAILED DESCRIPTION OF ILLUSTRATIVE EMBODIMENTS

The present invention provides novel macrocycles suitable for detecting (diagnosing) and treating target tissues, cells and pathogens. The compositions of the present invention possess novel chelating properties and cavity sizes, which enable them to stabilize metals in a range of typical and a typical oxidation states and coordination geometries. The compositions of the present invention find particular application in medical applications, such as Magnetic Resonance Imaging (MRI), Positron Emission Tomography (PET), Photodynamic Therapy (PDT), although the compositions have a wide variety of other applications.

In on embodiment, the present invention relates to N-heterocyclic carbene substituted porphyrins. That is, the compositions of the present invention are substituted porphyrins having at least one pyrrole ring of the porphyrin ring replaced by a N-heterocyclic carbene group. In other embodiments of the present invention, in addition to having at least one pyrrole group of the porphyrin ring replaced with a N-heterocyclic carbene group, at least one of the pyrrole groups of the porphyrin ring may also be replaced with a pyridine ring.

As those having ordinary skill in the art know, the term "porphyrin" refers to any of several physiologically active nitrogen-containing compounds. In general, a porphyrin compound includes four pyrrole rings, each ring containing a nitrogen atom and where two of the pyrrole rings also include replaceable hydrogen atoms. A porphyrin may be generally represented by the following formula:

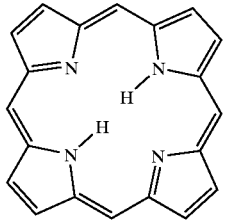

(I)

The synthesis of porphyrin isomers is known, where the nitrogen atom of one of the pyrrole rings that binds to a central metal atom to form a metal complex is replaced with a carbon atom. These porphyrin isomers, referred to as carbaporphyrins, N-confused porphyrins, or inverted porphyrins, may be represented by the following formula:

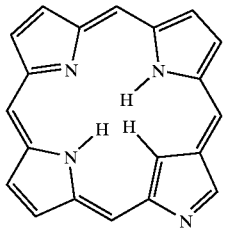

(II)

N-confused porphyrins as shown in Formula II, above, have a multivalent nature as a metal ligand and are known to complex with metal atoms in the +2 and +3 oxidation states to form neutral square planar complexes, as shown in the following formulas:

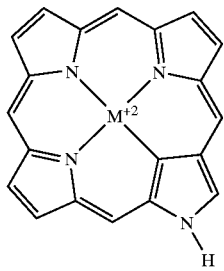

(III)

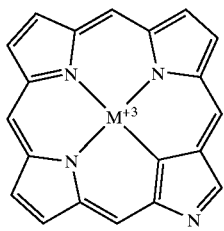

(IV)

Doubly N-confused porphyrins may also be synthesized and are able to form metal complexes with metals in the +3 oxidation state, as shown by the following formula:

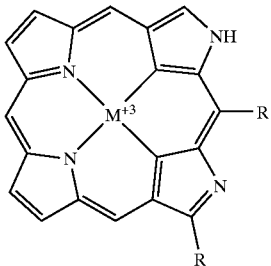

(V)

The N-heterocyclic carbene substituted porphyrins and porphyrinoids of the present invention may be broadly represented by the following formulas:

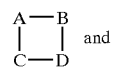

(VI)

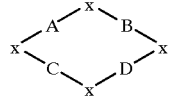

(VII)

where formulas VI and VII, A-D may be the same or different and may be selected from one of the following formulas, with the proviso that at least one of A-D is N-heterocyclic carbene:

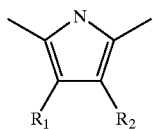

(VIII)

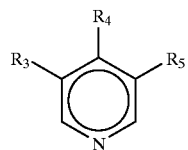

(IX)

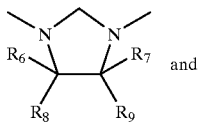

(Xa)

and

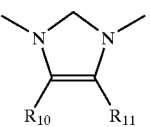

(Xb)

where $R_1$–$R_{11}$ may be hydrogen and organic groups including alkyl, cyclo alkyl, substituted cycloalkyl, alkenyl, cycloalkenyl, substituted cycloalkenyl, alkynyl, aryl, substituted aryl, arylalkyl, alkylaryl, and alkoxy, where each group preferably contains from 1 carbon atom to about 10 carbon atoms, preferably containing from 1 carbon atom to about 6 carbon atoms;

where x may be $CR_{12}$ or $CR_{13}R_{14}$, where $R_{12}$, $R_{13}$ and $R_{14}$ may be hydrogen and organic groups including alkyl, cyclo alkyl, substituted cycloalkyl, alkenyl, cycloalkenyl, substitute cycloalkenyl, alkynyl, aryl, substituted aryl, arylalkyl, alkylaryl, and alkoxy, where each group preferably contains from 1 carbon atom to about 10 carbon atoms, preferably containing from 1 carbon atom to about 6 carbon atoms.

The N-heterocyclic carbene substituted expanded porphyrins and expanded porphyrinoids of the present invention may be broadly represented by the following formulas:

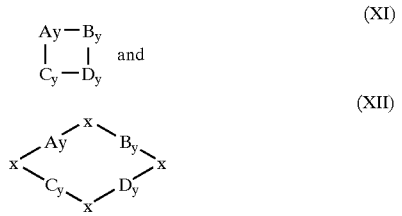

where formulas XI and XII, A-D may be the same or different and may be selected from one of the following formulas, with the proviso that at least one of A-D is N-heterocyclic carbene:

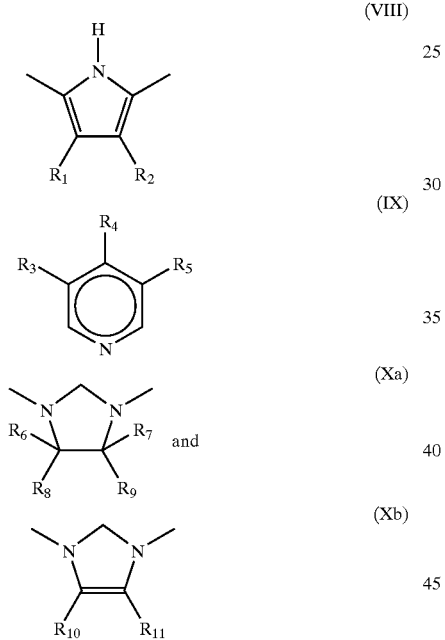

where $R_1$–$R_{11}$ may be hydrogen and organic groups including alkyl, cyclo alkyl, substituted cycloalkyl, alkenyl, cycloalkenyl, substituted cycloalkenyl, alkynyl, aryl, substituted aryl, arylalkyl, alkylaryl, and alkoxy, where each group preferably contains from 1 carbon atom to about 10 carbon atoms, preferably containing from 1 carbon atom to about 6 carbon atoms;

where x may be $CR_{12}$ or $CR_{13}R_{14}$, where $R_{12}$, $R_{13}$ and $R_{14}$ may be hydrogen and organic groups including alkyl, cyclo alkyl, substituted cycloalkyl, alkenyl, cycloalkenyl, substitute cycloalkenyl, alkynyl, aryl, substituted aryl, arylalkyl, alkylaryl, and alkoxy, where each group preferably contains from 1 carbon atom to about 10 carbon atoms, preferably containing from 1 carbon atom to about 6 carbon atoms; and where Ay, By, Cy and Dy is 1 or greater, with the proviso that at least one of Ay, By, Cy and Dy is at least 2.

The following examples are set forth to describe the N-heterocyclic substituted carbene porphyrin and porphyrinoid compositions of the present invention in further detail. The examples are intended to be illustrative, and should not be construed as limiting the scope of the present invention in any manner.

In one embodiment, at least one pyrrole ring of the porphyrin is replaced with a N-heterocyclic carbene group. The composition of this embodiment may be represented by any one of the following formulas:

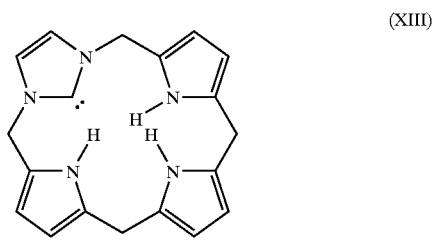

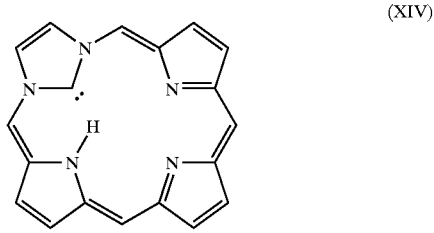

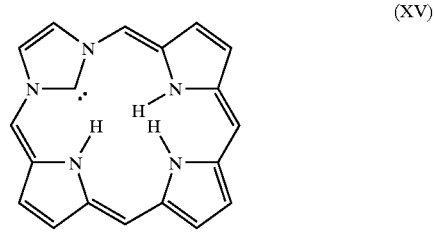

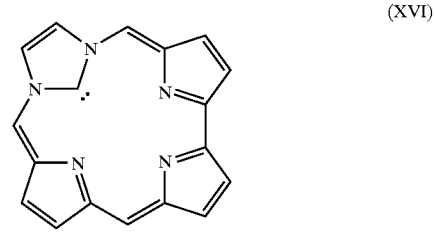

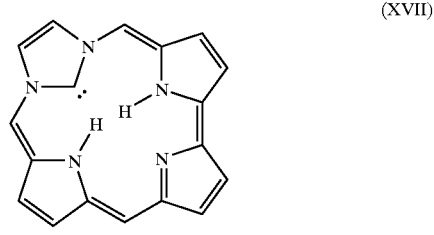

In another embodiment, two of the pyrrole rings of the porphyrin compound have been replaced with N-heterocyclic carbene groups. The compounds having two pyrrole rings replaced with N-heterocyclic carbene groups may be represented by any one of the following formulas:

(XVIII)

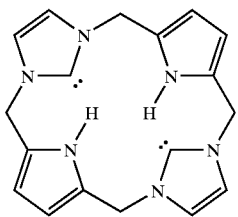

(XIX)

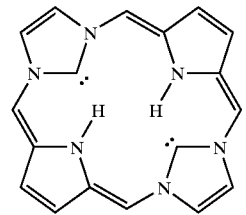

(XX)

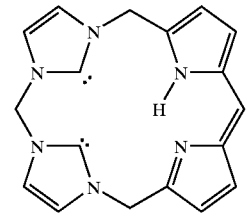

(XXI)

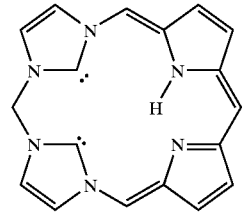

(XXII)

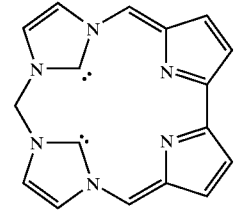

In another embodiment, three pyrrole rings of the porphyrin compound have been replaced with N-heterocyclic carbene groups. The compounds have three N-heterocyclic carbene groups may be represented by the following formula:

(XXIII)

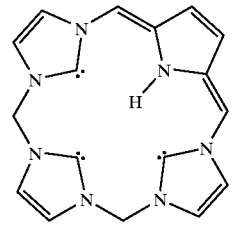

In another embodiment, four pyrrole rings of the porphyrin compound have been replaced with N-heterocyclic carbene groups. The compositions having four pyrrole rings of the porphyrin compound have been replaced with N-heterocyclic carbene groups may be represented by the following formula:

(XXV)

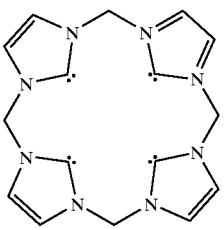

In another embodiment, the present invention provides compositions wherein at least one of the pyrrole rings of the porphyrin compound is replaced with a N-heterocyclic carbene group and at least one other pyrrole rings is replaced with a pyridine ring. The compositions having at least one of the pyrrole rings of the porphyrin compound is replaced with a N-heterocyclic carbene group and at least one other pyrrole ring is replaced with a pyridine ring may be represented by any one of the following formulas:

(XXVI)

(XXVII)

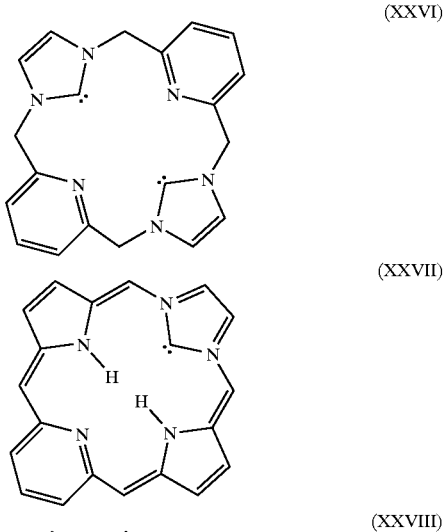

(XXVIII)

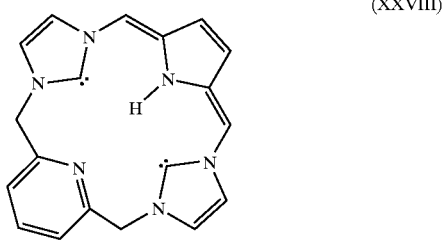

(XXIX)

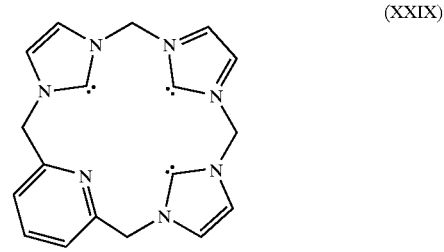

While the present invention has been described with respect to the substitution of porphyrins with at least one N-heterocyclic carbene group, the compositions and processes described herein also encompass other tetrapyrrolic macrocycles, such as the larger aromatic pyrrole-containing systems, referred to as "expanded porphyrins".

The term expanded porphyrin and expanded porphyrinoids refer to those large aromatic pyrrole-containing systems that generally contain more than four rings that constitute the macrocycle. As for the porphyrin systems, at least one pyrrole ring of an expanded porphyrin or expanded porphyrinoid can be replaced with a N-heterocyclic carbene group to form a N-heterocyclic carbene expanded porphyrin or a N-heterocylic carbene substituted expanded porphyrinoid.

In one embodiment, at least one pyrrole ring of the expanded porphyrin sapphyrin may be replaced by a N-heterocylic carbene group. Sapphyrin is represented by the following formula:

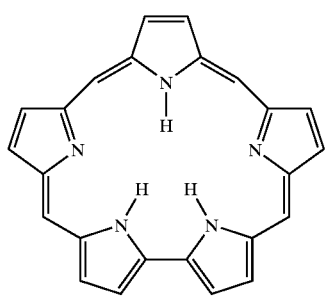
(XXX)

Compounds of the present invention having at least one pyrrole ring of the expanded porphyrin sapphyrin replaced by a N-heterocylic carbene group are represented by the following formulas:

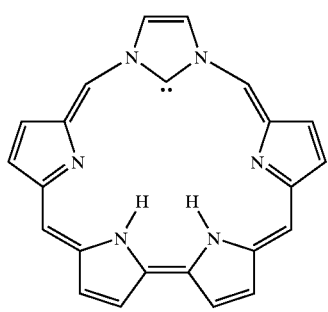
(XXXI)

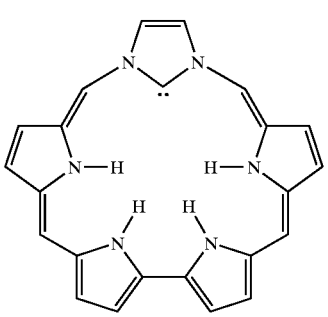
(XXXII)

In another embodiment, the present invention provides compositions having at least two pyrrole rings of the expanded porphyrin sapphyrin replaced with N-heterocyclic carbene groups. Compounds of the present invention having at least two pyrrole rings of the expanded porphyrin sapphyrin replaced by N-heterocyclic carbene groups are represented by the following formulas:

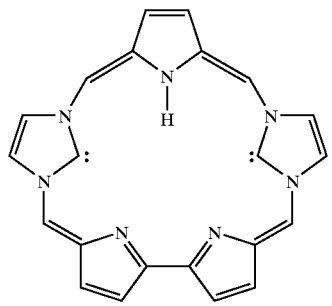
(XXXIII)

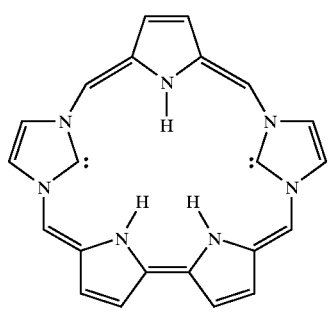
(XXXIV)

In another preferred embodiment, at least one pyrrole ring of the expanded porphyrin pentaphyrin is replaced by a N-heterocylic carbene group. The expanded porphyrin pentaphyrin is represented by the following formula:

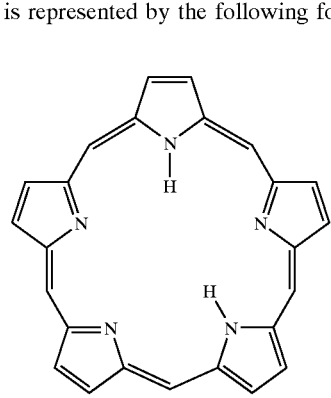
(XXXV)

In one embodiment, at least one pyrrole ring of the expanded porphyrin pentaphyrin has been replaced with a N-heterocyclic carbene group. Compositions of the present invention having at least one pyrrole ring of the expanded porphyrin pentaphyrin has been replaced with a N-heterocyclic carbene group are represented by the following formulas:

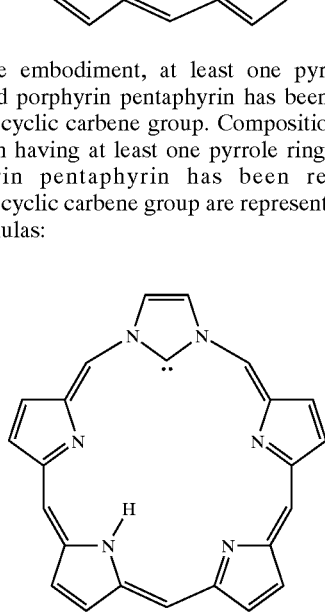
(XXXVI)

(XXXVII)

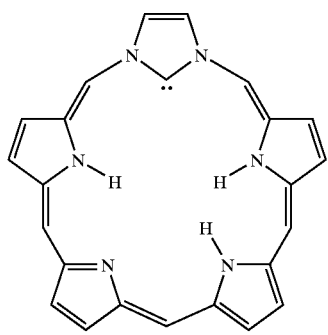

In another embodiment, at least two pyrrole rings of the expanded porphyrin pentaphyrin has been replaced with a N-heterocyclic carbene groups. Compositions of the present invention having at least two pyrrole rings of the expanded porphyrin pentaphyrin has been replaced with a N-heterocyclic carbene groups is represented by the following formula:

(XXXVIII)

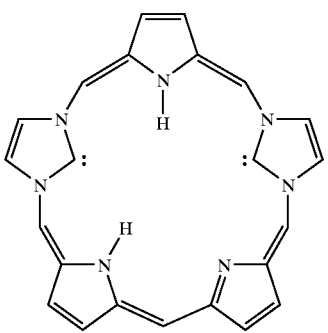

In another preferred embodiment, at least one pyrrole ring of the expanded porphyrin hexaphyrin is replaced by a N-heterocylic carbene group. Hexaphyrin is represented by the following formula:

(XXXIX)

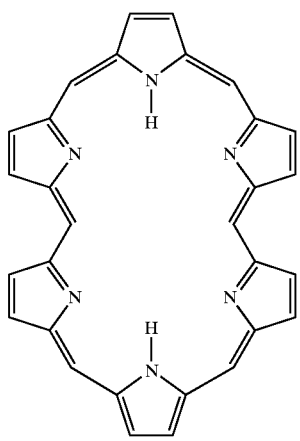

In one embodiment, at least one pyrrole ring of the expanded porphyrin hexaphyrin is replaced by a N-heterocyclic carbene group. Compositions of the present invention at least one pyrrole ring of the expanded porphyrin hexaphyrin is replaced by a N-heterocyclic carbene group are represented by the following formula:

(XXXX)

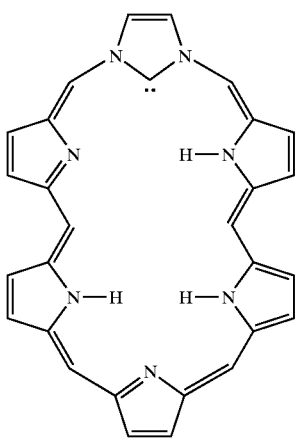

In another embodiment, at least two pyrrole rings of the expanded porphyrin hexaphyrin is replaced by N-heterocyclic carbene group. Compositions of the present invention at least two pyrrole rings of the expanded porphyrin hexaphyrin are replaced by N-heterocyclic carbene groups are represented by the following formulas:

(XXXXI)

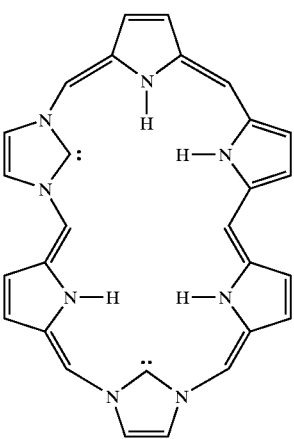

(XXXXII)

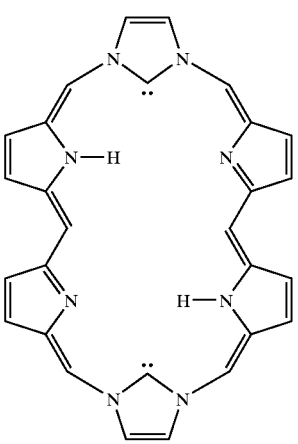

(XXXXIII)

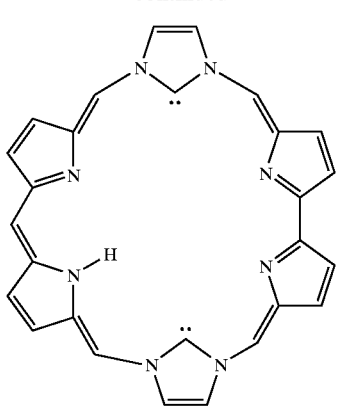

(XXXXIV)

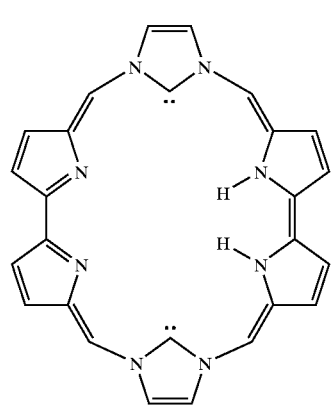

In another embodiment, at least three pyrrole rings of the expanded porphyrin hexaphyrin are replaced by N-heterocyclic carbene groups. Compositions of the present invention at least three pyrrole rings of the expanded porphyrin hexaphyrin are replaced by N-heterocyclic carbene groups are represented by the following formula:

(XXXXV)

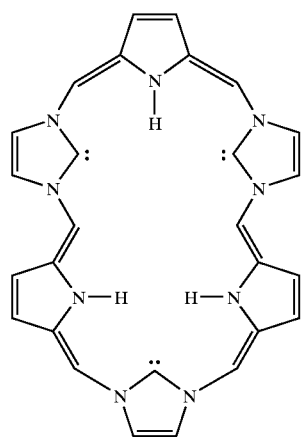

While the present invention has been illustrated in further detail with reference to tetrapyrrolic porphyrin and the expanded porphyrins sapphryin, pentaphyrin and hexaphyrin, it should be noted that the present invention is not limited to those expanded porphyrins described herein. The present invention, therefore, includes other expanded porphyrins in which at least one pyrrole ring is replaced by N-heterocyclic carbene groups.

The N-heterocyclic carbene substituted porphyrins and N-heterocyclic carbene substituted porphyrinoids of the present invention are useful as ligands to form ligand-metal complexes with a selected or desired metal atom or atoms.

The metal complexes of the present invention include a N-heterocyclic carbene substituted porphyrin or N-heterocyclic carbene substituted porphyrinoid and at least one metal atom bonded to the N-heterocyclic carbene substituted porphyrin or N-heterocyclic carbene substituted porphyrinoids. The metal complexes of this embodiment may be broadly represented by the following formulas:

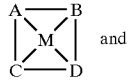 and (XXXXVI)

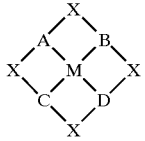 (XXXXVII)

where for formulas XXXXVI and XXXXVII, A-D may be the same or different and may be selected from one of the following formulas, with the proviso that at least one of A-D is N-heterocyclic carbene:

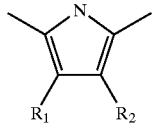 (VIII)

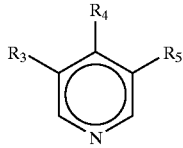 (IX)

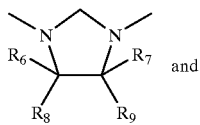 and (Xa)

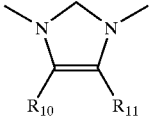 (Xb)

where $R_1$–$R_{11}$ may be hydrogen and organic groups including alkyl, cyclo alkyl, substituted cycloalkyl, alkenyl, cycloalkenyl, substituted cycloalkenyl, alkynyl, aryl, substituted aryl, arylalkyl, alkylaryl, and alkoxy, where each group preferably contains from 1 carbon atom to about 10 carbon atoms, preferably containing from 1 carbon atom to about 6 carbon atoms;

where x may be $CR_{12}$ or $CR_{13}R_{14}$, where $R_{12}$, $R_{13}$ and $R_{14}$ may be hydrogen and organic groups including alkyl, cyclo alkyl, substituted cycloalkyl, alkenyl, cycloalkenyl, substitute cycloalkenyl, alkynyl, aryl, substituted aryl, arylalkyl, alkylaryl, and alkoxy, where each group preferably contains from 1 carbon atom to about 10 carbon atoms, preferably containing from 1 carbon atom to about 6 carbon atoms; and where M is a metal.

The metal complexes of this embodiment, which in clued at least one metal atom bonded to a N-heterocyclic carbene substituted expanded porphyrin or expanded porphyrinoids may be broadly represented by the following formulas:

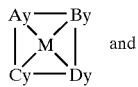
(XXXXVIII)

and

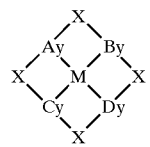
(XXXXIX)

where formulas XXXXVIII and XXXXIX, A-D may be the same or different and may be selected from one of the following formulas, with the proviso that at least one of A-D is N-heterocyclic carbene:

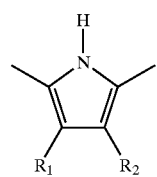
(VIII)

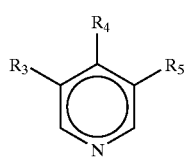
(IX)

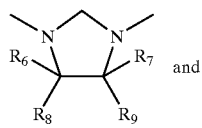
(Xa)

and

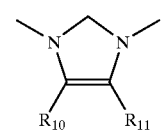
(Xb)

where $R_1$–$R_{11}$ may be hydrogen and organic groups including alkyl, cyclo alkyl, substituted cycloalkyl, alkenyl, cycloalkenyl, substituted cycloalkenyl, alkynyl, aryl, substituted aryl, arylalkyl, alkylaryl, and alkoxy, where each group preferably contains from 1 carbon atom to about 10 carbon atoms, preferably containing from 1 carbon atom to about 6 carbon atoms;

where x may be $CR_{12}$ or $CR_{13}R_{14}$, where $R_{12}$, $R_{13}$ and $R_{14}$ may be hydrogen and organic groups including alkyl, cyclo alkyl, substituted cycloalkyl, alkenyl, cycloalkenyl, substitute cycloalkenyl, alkynyl, aryl, substituted aryl, arylalkyl, alkylaryl, and alkoxy, where each group preferably contains from 1 carbon atom to about 10 carbon atoms, preferably containing from 1 carbon atom to about 6 carbon atoms; and where Ay, By, Cy and Dy is 1 or greater, with the proviso that at least one of Ay, By, Cy and Dy is at least 2; and where M is a metal.

Metal M may be selected from all of the main group metals and transition metals may to be complexed with the N-heterocyclic carbene substituted porphyrin and porphyrinoid ligands to form metal complexes. Additionally, isotopes of the main group metals and transition metals may be complexed with the ligands of the present invention to provides metal complexes.

While the known doubly N-confused porphyrins form neutral metal complexes with metals in +2 and +3 oxidation states, the carbene porphyrins, carbene porphyrinoids, expanded carbeneporphyrins and expanded carbeneporphyrinoids have the capability of forming neutral metal complexes with metals in the 0, +1, +2, +3, +4, and +5 oxidation states. Because of the strong complexing ability of N-heterocyclic carbenes, the compositions of the present invention, the carbeneporphyrins and expanded carbeneporphyrins, bind more strongly to the central metal atom in comparison to porphyrins and confused porphyrins without substitution with N-heterocyclic carbene groups.

The N-heterocyclic carbene porphyrins, including the N-heterocyclic carbene porphyrinoids, and the expanded N-heterocyclic carbene porphyrins, including the expanded N-heterocyclic carbene porphyrinoids, of the present invention may be complexed with metal atoms to form ligand-metal complexes. Virtually of the of the main group metals and transition metals may be complexed with the N-heterocyclic carbene porphyrins, including the N-heterocyclic carbene porphyrinoids, and the expanded N-heterocyclic carbene porphyrins, including the expanded N-heterocyclic carbene porphyrinoids, of the present invention to form ligand-metal complexes.

Suitable metal atoms, M, that may be complexed with the N-heterocyclic carbene porphyrins and N-heterocyclic carbene porphyrinoids of the present invention include, but are not limited to, all group IIA metals, group IIA metals, group IIIA metals, group IVA metals, group VA metals, group VIA metals, group VIIA metals, and group VIIIA metals. The group IVB metals Si, Ge, SN and Pb may be complexed with the N-heterocyclic carbene porphyrins and N-heterocyclic carbene porphyrinoids to form ligand-metal complexes. The group VB metals P, As, Sb and Bi may be complexed with N-heterocyclic carbene porphyrins and N-heterocyclic carbene porphyrinoids to form ligand-metal complexes. The group VIB metals Te and Po may be complexed with N-heterocyclic carbene porphyrins and N-heterocyclic carbene porphyrinoids to form ligand-metal complexes. The group VIIB metal At may be complexed with N-heterocyclic carbene porphyrins and N-heterocyclic carbene porphyrinoids to form ligand-metal complexes. Additionally, the lanthanides and the actinides may be complexed with the N-heterocyclic carbene porphyrins and N-heterocyclic carbene porphyrinoids of the present invention to form ligand-metal complexes.

Preferably, the metals that may be used to form metal complexes with the ligands include those metals that have particular application in MRI, PET and PDT. These metals include, but are not limited to, Be(II), Mg(II), Ca(II), Sr(II), Ba(II), B(III), Al(III), Ga(III), In(III), Cr(O), Fe(O), Ni(O), Mo(O), Ru(O), Pd(O), Pt(O), Re(I), Cr(I), Mn(I), Fe(I), Co(I), Ni(I), Cu(I), Rh(I), Ag(I), Re(I), Ir(I), Au(I), V(I), Cr(II), Fe(II), Co(II), Ir(III), Ti(IV), V(IV), Zr(IV), Nb(IV), Hf(IV), Ta(IV), Mo(IV), W(VI), Re(VII), La(II), La(III), Nd(III), Sm(II), Er(III), Sm(II) and Yb(II). Suitable examples of these metals having particular application in MRI and are, therefore, useful in the present invention include, but are not limited to, Fe(III), Mg(II), Mn(II), and Gd(III). More preferably, Gd(III) will be used to form ligand-metal complexes that find particular use in MRI applications. Useful radioisotopes that can be complexed with the N-heterocyclic carbene substituted porphyrins and porphyrinoids in clued, but are not limited to, $^{67}$Cu, $^{105}$Rh, $^{111}$Ag, $^{117}$Sn, $^{186}$Re, $^{149}$Pm, $^{153}$Sm, $^{166}$Ho and $^{177}$Lu. $^{111}$Ag is a preferred radioisotope that can be complexed with the N-heterocyclic carbenes substituted ligands of the present invention.

The present invention also provides processes for the preparation for of the N-heterocyclic carbene substituted porphyrins and N-heterocyclic carbene substituted porphyrinoids of the present invention, including the preparation of N-heterocyclic carbene substituted expanded porphyrins and N-heterocyclic carbene substituted expanded porphyrinoids.

The present invention further provides a process for the preparation of a complex of the ligands of the present invention with a desired metal to produce a ligand-metal complex.

Preparation of N-heterocyclic Carbene Porphyrins and Porphyrinoids

The following examples are set forth to describe the preparation of the compositions of the present invention in further detail and to illustrate the methods of the present invention. However, the examples should not be construed as limiting the present invention in any manner.

In the following synthetic procedures the synthesis of the ligands of the present invention is described. However, ligands can be synthesized with various functional groups on the exterior of the rings in order to give the overall complex sufficient solubility, lipophilicity and targeting properties. Pyrroles and imidazoles serve as the fundamental building blocks in the procedures discussed below.

Synthesis of Monocarbeneporphyrin

Below is a reaction scheme for the synthesis of mono N-heterocyclic carbene substituted porphyrin:

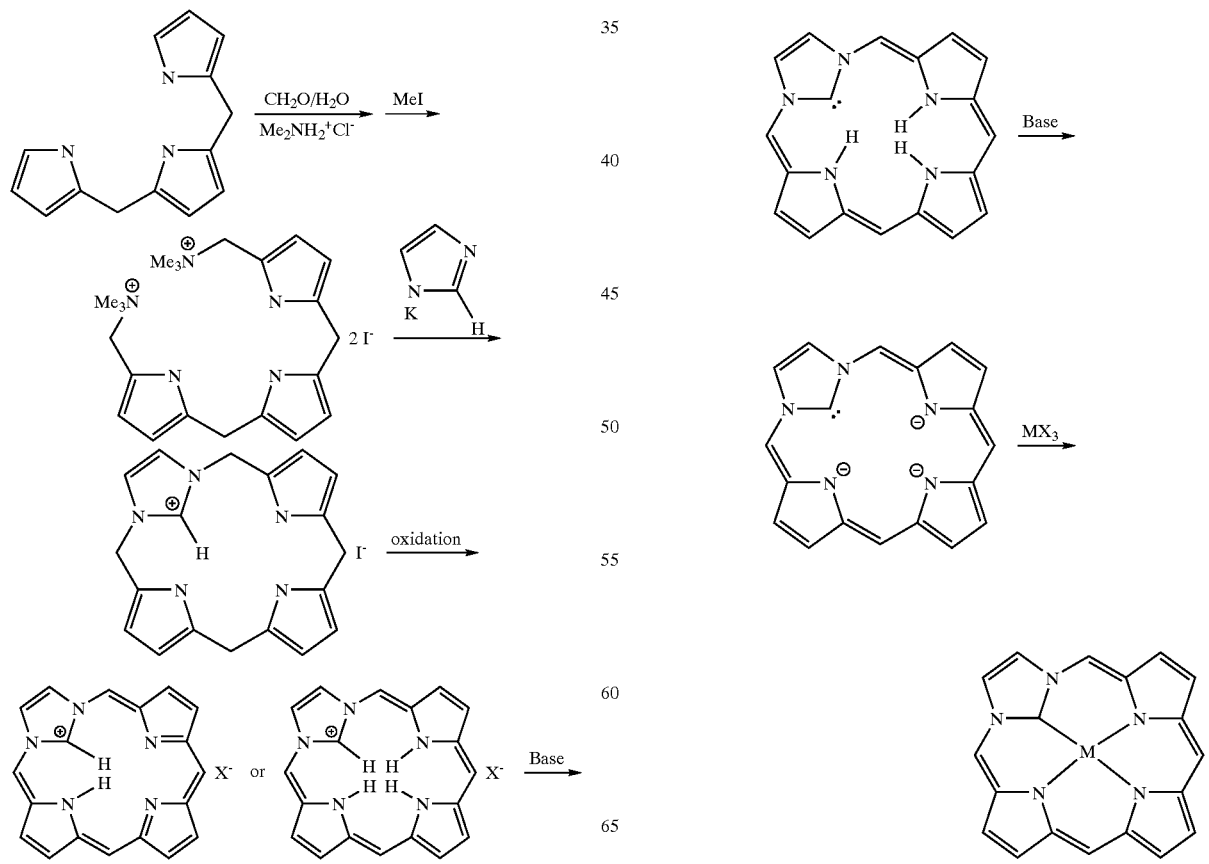

Synthesis of Dicarbeneporphyrinoids
Below is a reaction scheme for the synthesis of di N-heterocyclic carbene substituted porphyrinoids:
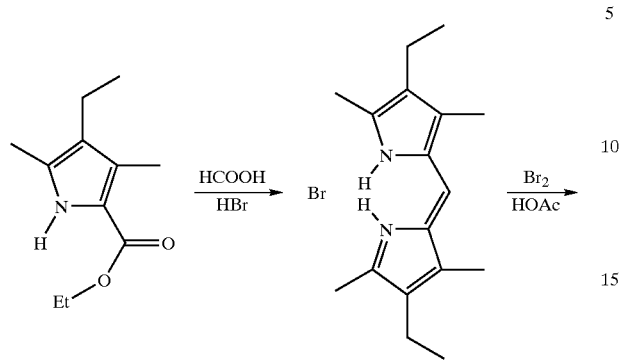
Synthesis of Tricarbeneporphyrinoids
Below is a reaction scheme for the synthesis of tricarbeneporphyrinoids and ligand-metal complexes of tricarbeneporphyrinoids and a metal:
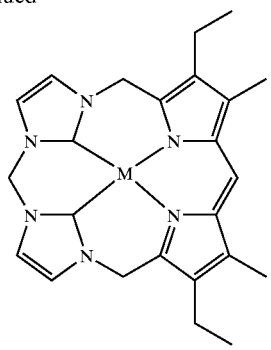
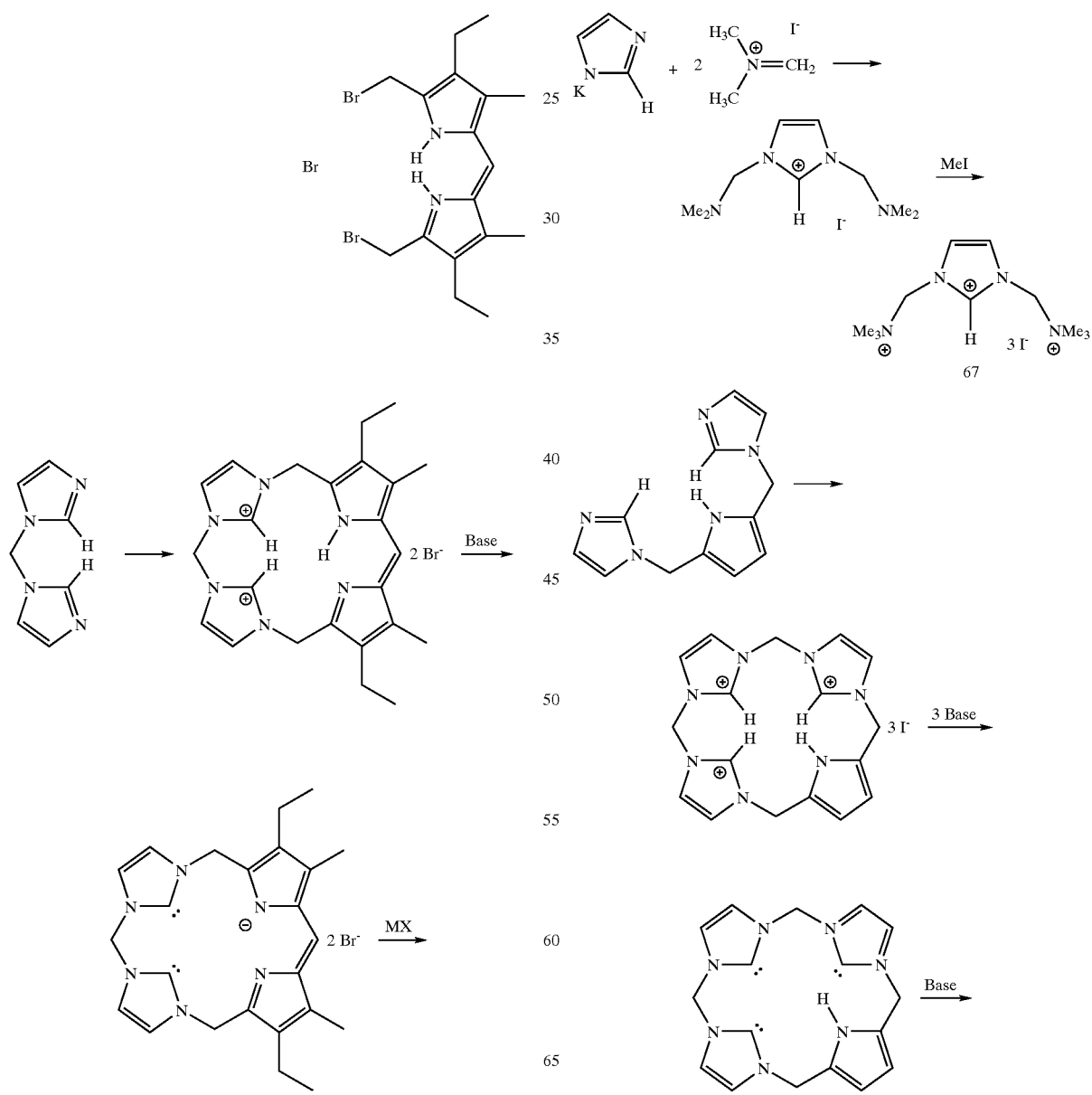

Synthesis of Tetracarbeneporphyrinoids

Below is a reaction scheme for the synthesis of tetracarbeneporphyrinoids and ligand-metal complexes of tetracarbeneporphyrinoids and a metal:

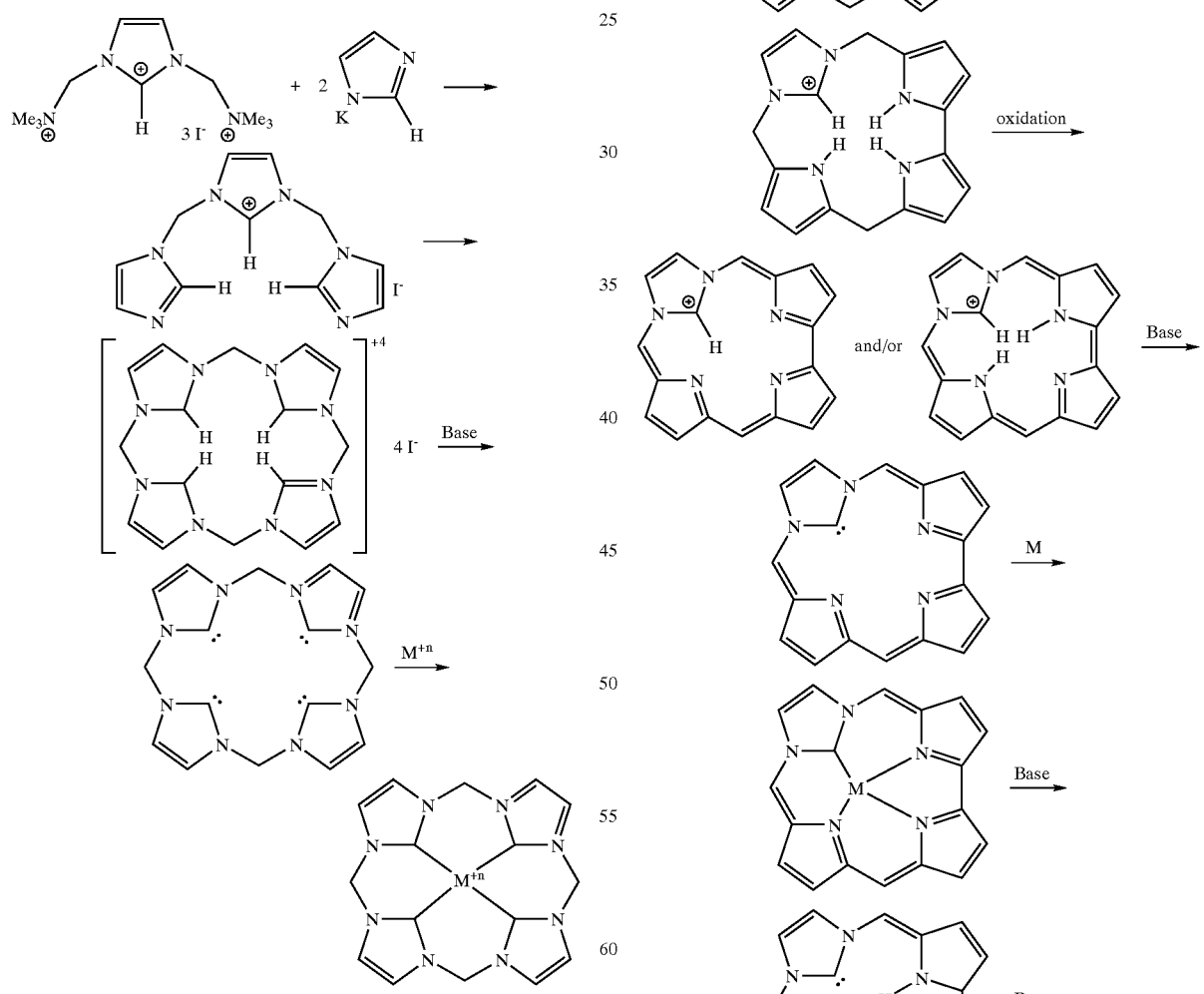

Synthesis of Carbene Corrole Porphyrins

Below is a reaction scheme for the synthesis of carbene corrole porphyrins and ligand-metal complexes of carbene corrole porphyrins and a metal:

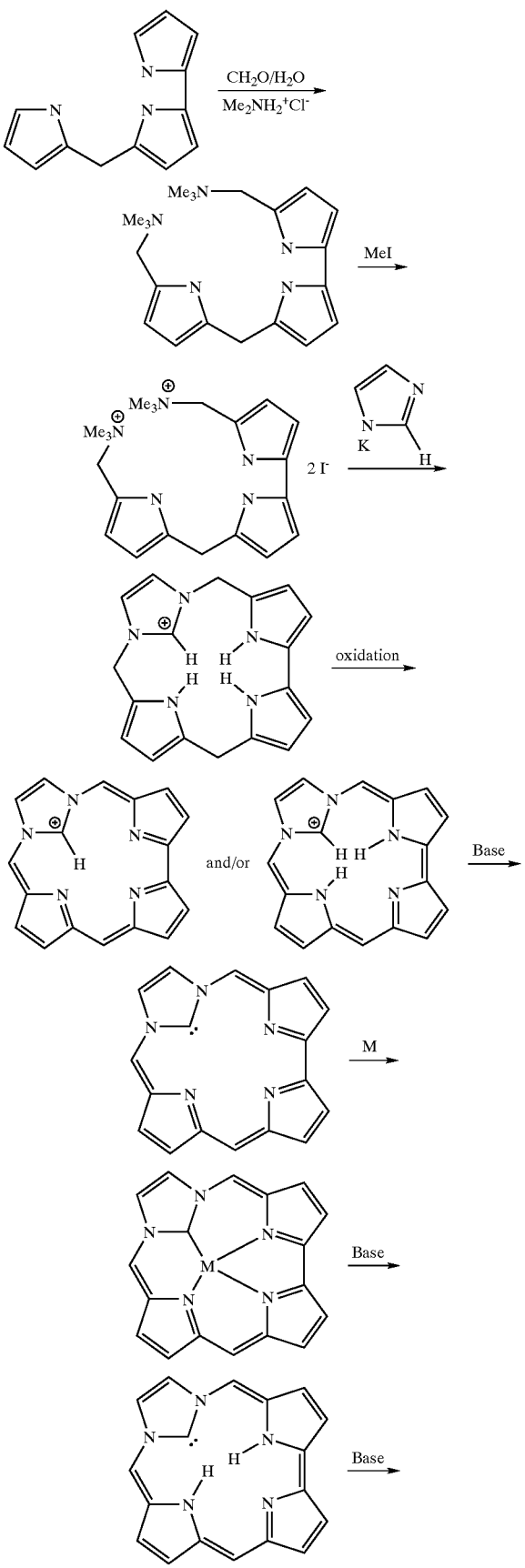

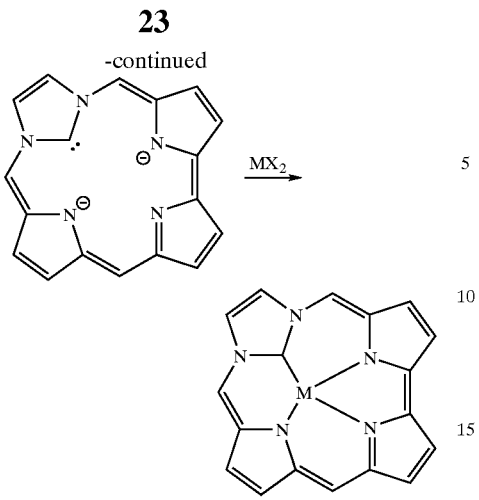
Synthesis of Expanded Monocarbenepentaphyrin
Below is a reaction scheme for the synthesis of mono N-heterocylic carbene substituted expanded porphyrin:
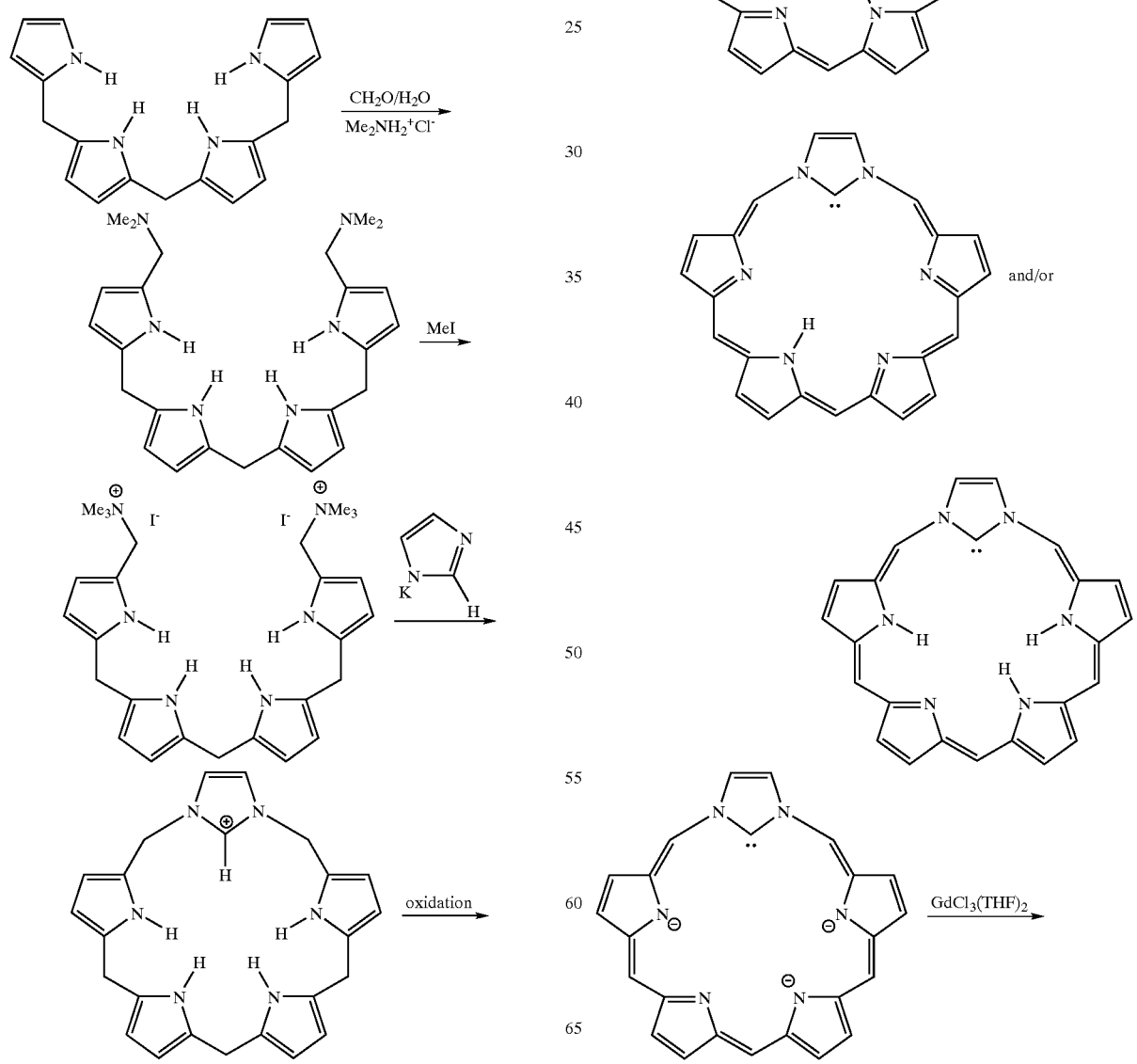
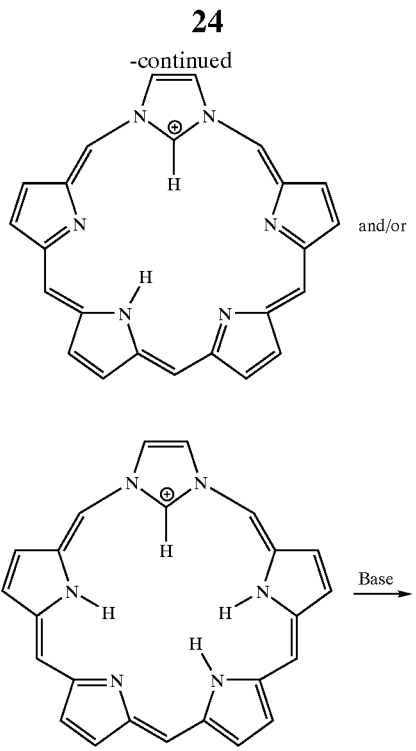

25
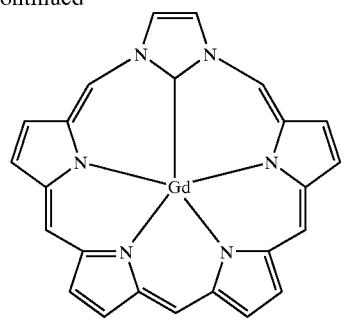
Synthesis of Dicarbenepentaphyrin
Below is a reaction scheme for the synthesis of di-N-heterocylic carbene substituted expanded porphyrin:
26
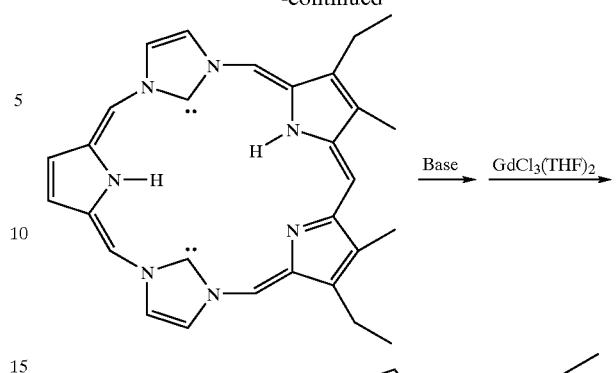
Synthesis of di-N-heterocyclic carbenehexaphyrins
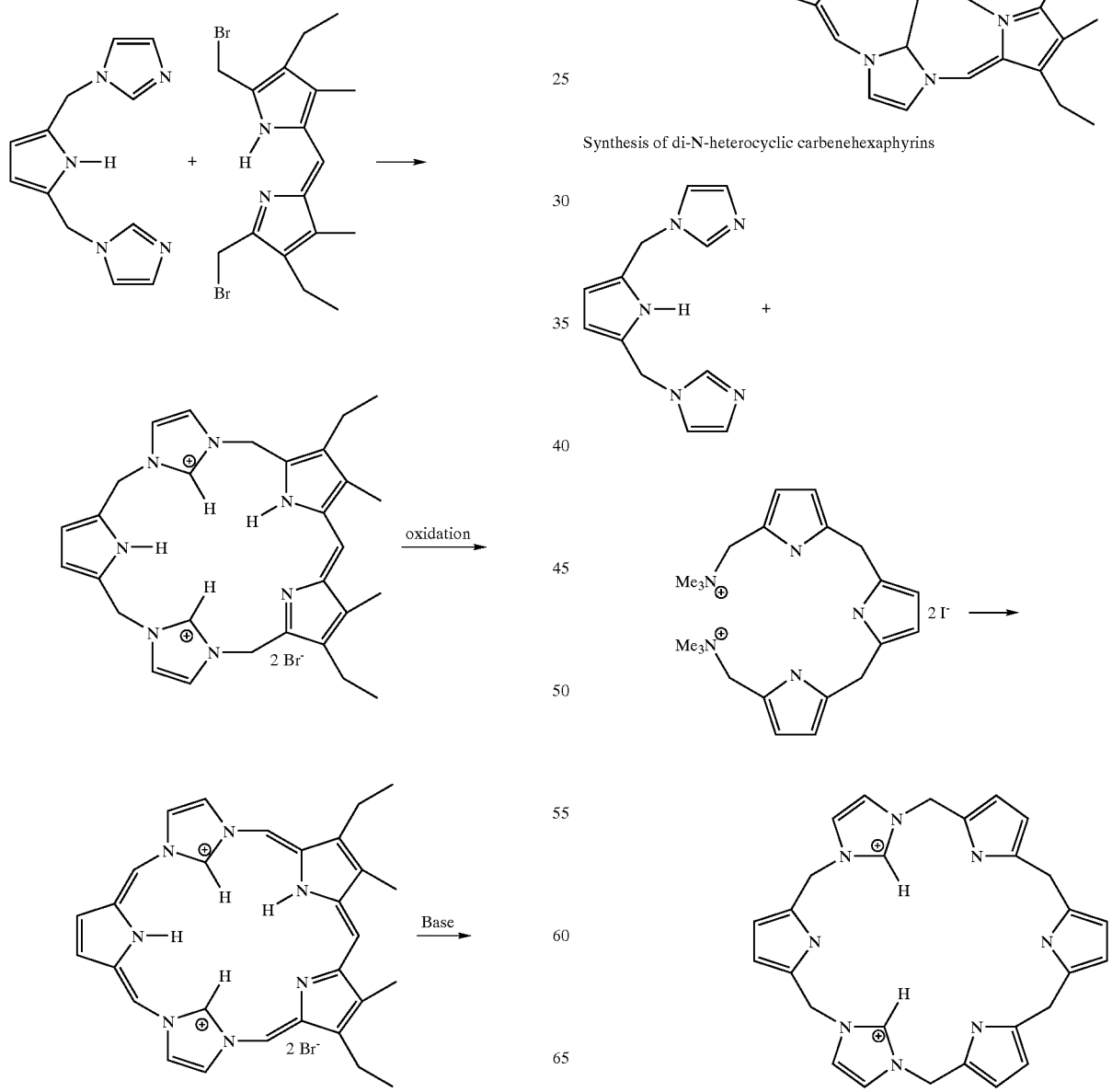

Synthesis of Tricarbenehexaphyrin
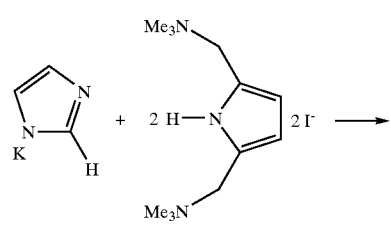
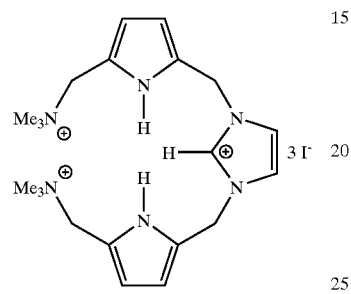
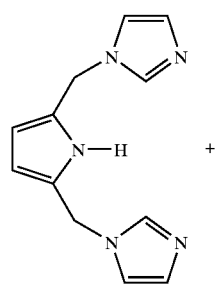
+
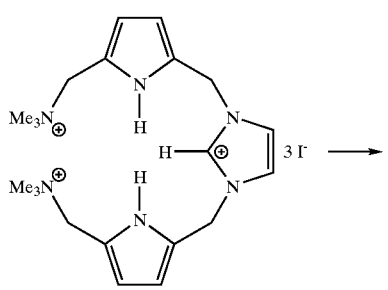
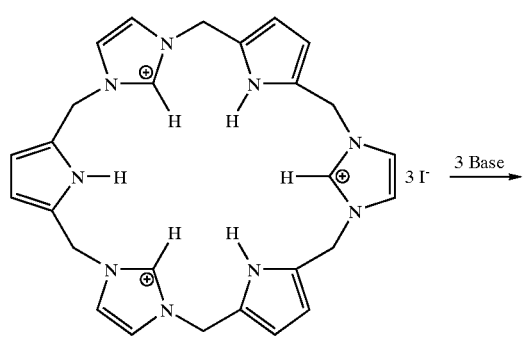 3 Base →
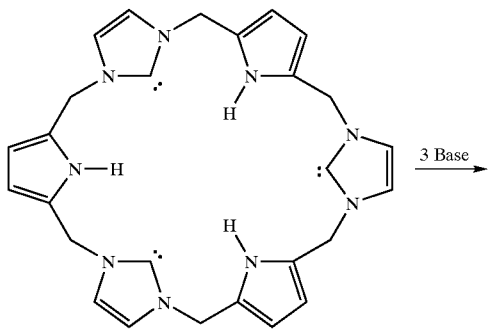
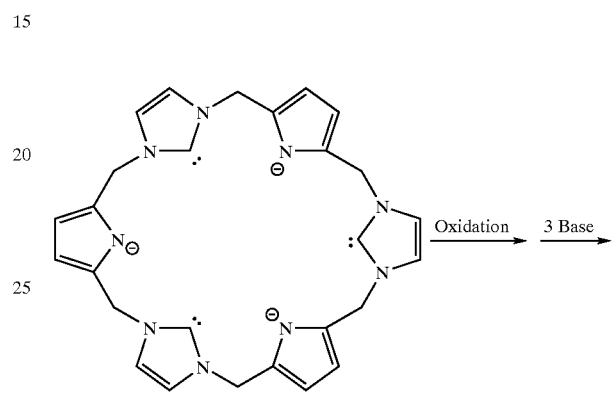 3 Base →
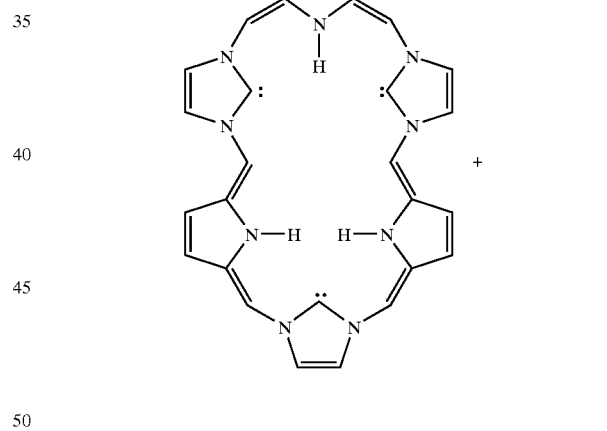 Oxidation, 3 Base →
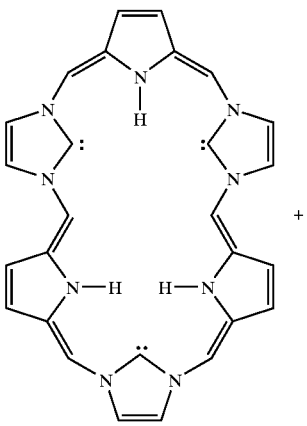 +
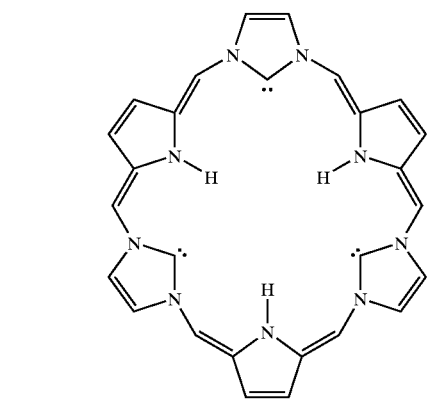

It should be noted that the term "N-heterocyclic carbene porphyrin" refers to porphyrins that have at least one pyrrole group replaced by a N-heterocyclic carbene and having unsaturated bonds linking the groups of the ring together or a mixture of saturated and unsaturated bonds linking the group of the ring together. The term "N-heterocyclic carbene porphyrinoid" refers to porphyrins that have at least one pyrrole group replaced by a N-heterocyclic carbene group and having saturated bonds linking the groups of the ring together.

In other embodiments, the N-heterocyclic carbene substituted porphyrins and porphyrinoids and metal complexes of the N-heterocyclic carbene substituted porphyrins and porphyrinoids may be further linked or bonded to a targeting moiety via a linker group. The targeting moiety may be selected to be specific to a receptor or protein located on a target tissue or cell. The targeting moiety further enables the ligand-metal complexes of the present invention to target specific tissue for diagnosis and treatment. In an alternative embodiment, the linker group and targeting moiety are dissociative, which enables the ligand-metal complex to diffuse out of the target tissue or cells and be removed from the patient's body.

Preparation of N-heterocyclic Carbene Porphyrins with Targeting Moiety

Below are reaction schemes for the synthesis of N-heterocyclic carbene substituted porphyrins having a targeting moiety bonded thereto:

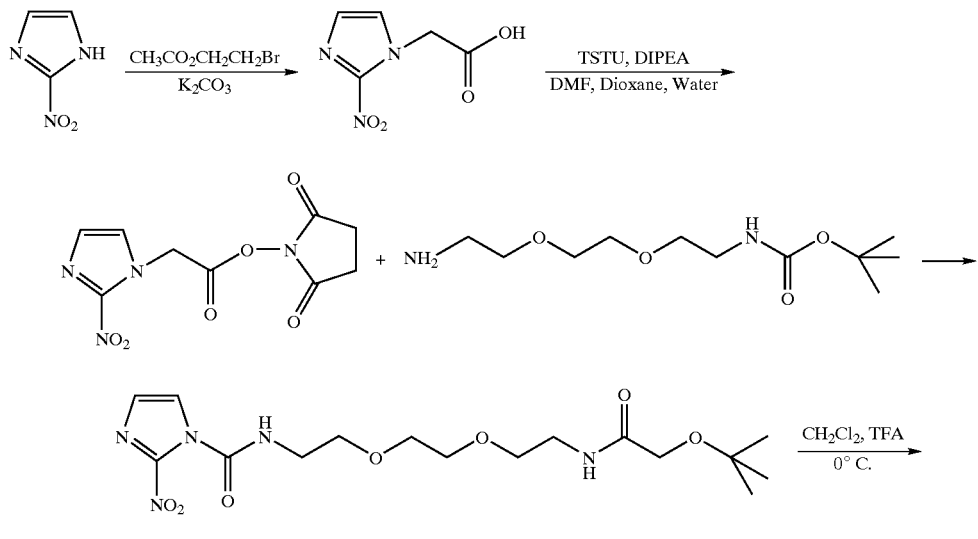

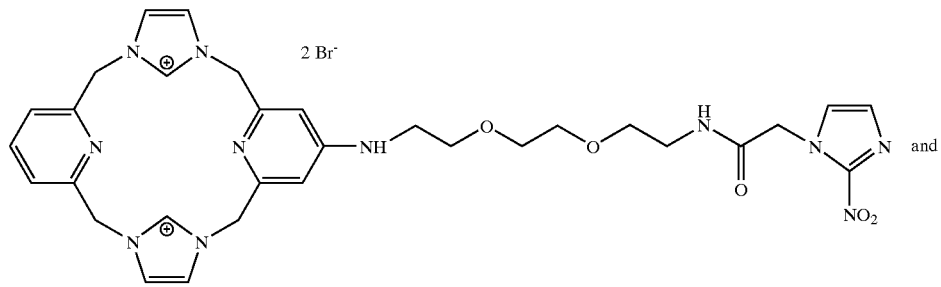

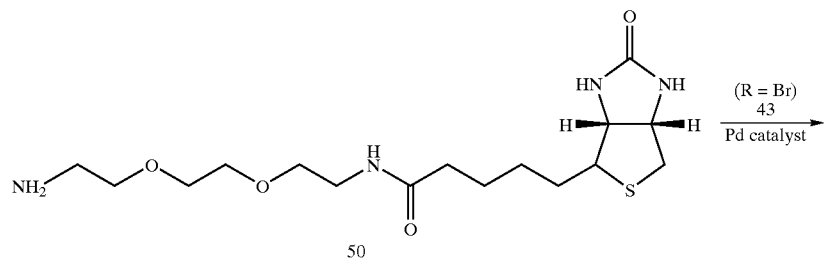

-continued

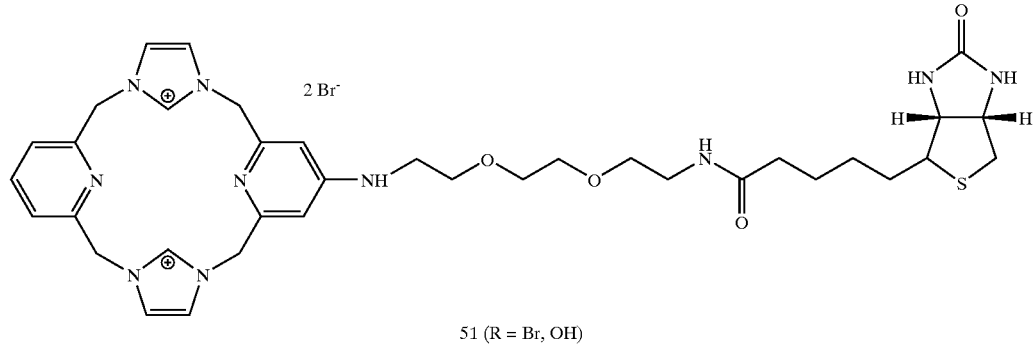

51 (R = Br, OH)

The targeting moiety is bonded to the N-heterocyclic carbene substituted porphyrin via a linker group. The linker group can be any organic group including, for example, organic radical groups and polymers. Suitable organic groups include alkyl, substituted alkyl, alkenyl, substituted alkenyl, alkynyl, substituted alkynyl, aryl, substituted aryl, arylalkyl, alkylaryl, alkoxy, amines, amides, and polyethers. The targeting moiety can be selected in order to optimize the solubility and lipophilicity of.

The N-heterocyclic carbene substituted ligands of the present invention, including the N-heterocyclic carbene substituted porphyrins and porphyrinoids, possess cavity sizes and chelating properties that enable the ligands to bind metal atoms more stringly than those macrocycles known in the prior art. The ability of the ligands of the present invention to bind more strongly to the metal atoms helps overcome the problems of dissociation of metal from the ligand while the metal complex is in a patient's body. As such, the ligands and metal complexes of the invention can be utilized as radioimaging agents and therapeutic radiopharmaceuticals for treating, for example, cancer. The metal complexes of the present invention can be used to recognize tumor-associated antigens and tumor specific antigens to deliver a therapeutic and cytotoxic agent to cancerous tissue and cells, while minimizing exposure of the cytotoxic agents to non-cancerous, healthy tissue and cells. Antibodies such as, for example, monoclonal antibodies that recognize tumor associated antigen or tumor specific antigen, are complexed with strepravidin and infused into a patient. The antibody recognizes the tumor associated antigen and associates with is, thereby localizing the streptavidin in the tumor tissue. Subsequently, the metal complexes of N-heterocyclic carbene substituted porphyrins or porphyrinoid, which have biotin bound thereto, are infused into the patient. The streptavidin binds the biotin and localizes the radionucleotide at the tumor tissue.

Based on the foregoing disclosure, it is therefore demonstrated that the objects of the present invention are accomplished by the N-heterocyclic carbene porphyrins and porphyrinoids described and processes for installation described herein. It should be appreciated that the present invention is not limited to the specific embodiments described above, but includes variations, modifications and equivalent embodiments.

We claim:

1. A composition of matter comprising a N-heterocylic carbene substituted porphyrin.

2. The composition of claim 1, wherein said N-heterocylic carbene substituted porphyrin has the following general formula:

(VI)

wherein A-D may be the same or different and may be selected from one of the following formulas, with the proviso that at least one of A-D is N-heterocyclic carbene:

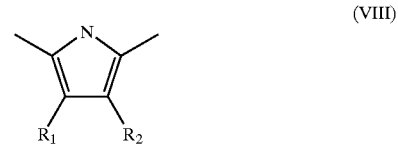

(VIII)

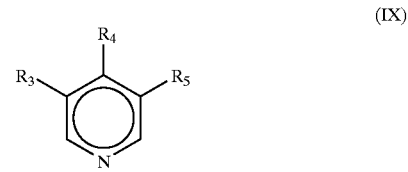

(IX)

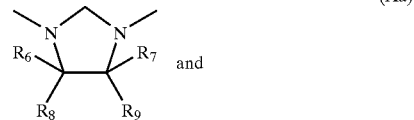

(Xa)

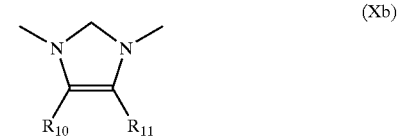

(Xb)

wherein $R_1$–$R_{11}$ may be hydrogen and organic groups including alkyl, cyclo alkyl, substituted cycloalkyl, alkenyl, cycloalkenyl, substituted cycloalkenyl, alkynyl, aryl, substituted aryl, arylalkyl, alkylaryl, and alkoxy.

3. The composition of matter of claim 2, wherein each of $R_1$–$R_{11}$ contains from 1 carbon atom to about 10 carbon atoms.

4. The composition of claim 3, wherein each of $R_1$–$R_{11}$ contains from 1 carbon atom to about 6 carbon atoms.

5. The composition of matter of claim 1, wherein said N-heterocylic carbene substituted porphyrin has the following general formula:

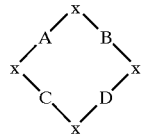
(VII)

wherein A-D may be the same or different and may be selected from one of the following formulas, with the proviso that at least one of A-D is N-heterocyclic carbene:

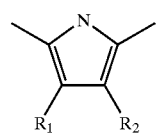
(VIII)

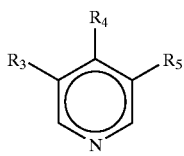
(IX)

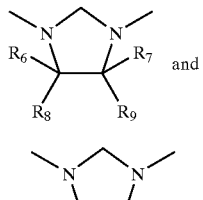
(Xa)

and

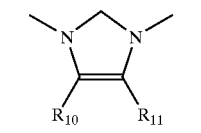
(Xb)

wherein $R_1$–$R_{11}$ may be hydrogen and organic groups including alkyl, cyclo alkyl, substituted cycloalkyl, alkenyl, cycloalkenyl, substituted cycloalkenyl, alkynyl, aryl, substituted aryl, arylalkyl, alkylaryl, and alkoxy;

wherein x may be $CR_{12}$ or $CR_{13}R_{14}$, where $R_{12}$, $R_{13}$ and $R_{14}$ may be hydrogen and organic groups including alkyl, cyclo alkyl, substituted cycloalkyl, alkenyl, cycloalkenyl, substitute cycloalkenyl, alkynyl, aryl, substituted aryl, arylalkyl, alkylaryl, and alkoxy.

6. The composition of matter of claim 5, wherein each of $R_1$–$R_{14}$ contains from 1 carbon atom to about 10 carbon atoms.

7. The composition of claim 6, wherein each of $R_1$–$R_{14}$ contains from 1 carbon atom to about 6 carbon atoms.

8. The composition of claim 1, wherein the N-heterocylic carbene substituted porphyrin is represented by the following formula:

(XI)

wherein A-D may be the same or different and may be selected from one of the following formulas, with the proviso that at least one of A-D is N-heterocyclic carbene:

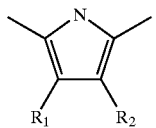
(VIII)

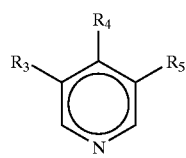
(IX)

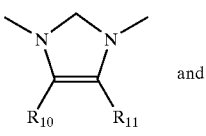
(Xb)

and

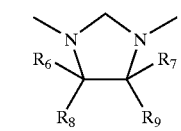
(Xa)

wherein $R_1$–$R_{11}$ may be hydrogen and organic groups including alkyl, cyclo alkyl, substituted cycloalkyl, alkenyl, cycloalkenyl, substituted cycloalkenyl, alkynyl, aryl, substituted aryl, arylalkyl, alkylaryl, and alkoxy, wherein Ay, By, Cy and Dy is 1 or greater with the proviso that at least one of Ay, By, Cy and Dy is at least 2.

9. The composition of matter of claim 8, wherein each of $R_1$–$R_{11}$ contains from 1 carbon atom to about 10 carbon atoms.

10. The composition of claim 9, wherein each of $R_1$–$R_{11}$ contains from 1 carbon atom to about 6 carbon atoms.

11. The composition of claim 1, wherein the N-heterocylic carbene substituted porphyrin is represented by the following formula:

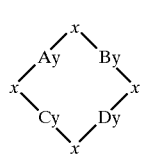
(VII)

wherein A-D may be the same or different and may be selected from one of the following formulas, with the proviso that at least one of A-D is N-heterocyclic carbene:

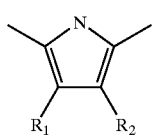
(VIII)

(IX)

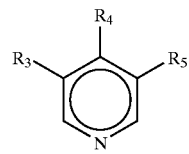

(Xa)

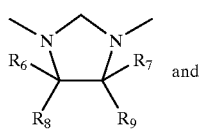
and (Xb)

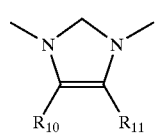

wherein $R_1$–$R_{11}$ may be hydrogen and organic groups including alkyl, cyclo alkyl, substituted cycloalkyl, alkenyl, cycloalkenyl, substituted cycloalkenyl, alkynyl, aryl, substituted aryl, arylalkyl, alkylaryl, and alkoxy, wherein Ay, By, Cy and Dy is 1 or greater with the proviso that at least one of Ay, By, Cy and Dy is at least 2; and wherein x may be $CR_{12}$ or $CR_{13}R_{14}$, where $R_{12}$, $R_{13}$ and $R_{14}$ may be hydrogen and organic groups including alkyl, cyclo alkyl, substituted cycloalkyl, alkenyl, cycloalkenyl, substitute cycloalkenyl, alkynyl, aryl, substituted aryl, arylalkyl, alkylaryl, and alkoxy.

12. The composition of matter of claim 11, wherein each of $R_1$–$R_{14}$ contains from 1 carbon atom to about 10 carbon atoms.

13. The composition of claim 12, wherein each of $R_1$–$R_{14}$ contains from 1 carbon atom to about 6 carbon atoms.

14. A metal complex comprising:
a N-heterocylic carbene substituted porphyrin; and
at least one metal atom bonded to N-heterocylic carbene substituted porphyrin.

15. The metal complex of claim 14, wherein said metal complex has the following general formula:

wherein A-D may be the same or different and may be selected from one of the following formulas, with the proviso that at least one of A-D is N-heterocyclic carbene:

(VIII)

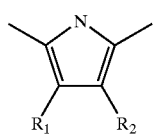

(IX)

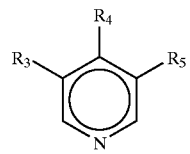

(Xa)

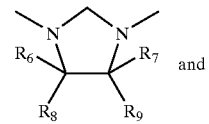
and (Xb)

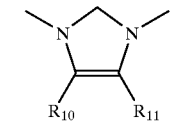

wherein $R_1$–$R_{11}$ may be hydrogen and organic groups including alkyl, cyclo alkyl, substituted cycloalkyl, alkenyl, cycloalkenyl, substituted cycloalkenyl, alkynyl, aryl, substituted aryl, arylalkyl, alkylaryl, and alkoxy;
and where M is a metal.

16. The metal complex of claim 15, wherein each of $R_1$–$R_{11}$ contains from 1 carbon atom to about 10 carbon atoms.

17. The metal complex of claim 16, wherein each $R_1$–$R_{11}$ contains from 1 carbon atom to about 6 carbon atoms.

18. The metal complex of claim 14, wherein said metal atom is selected from the group consisting of IIA metals, group IIA metals, group IIIA metals, group IVA metals, group VA metals, group VIA metals, group VIIA metals, and group VIIIA metals, group IVB metals, group VB metals, group VIB metals, VIIB metals, lanthanides and actinides.

19. The metal complex of claim 18, wherein the group IVB metals are selected from the group consisting of Si, Ge, SN and Pb.

20. The metal complex of claim 18, wherein the group VIB metals are selected from the group consisting of Te and Po.

21. The metal complex of claim 18, wherein the group VB metals are selected from the group consisting of P, As, Sb and Bi.

22. The metal complex of claim 18, wherein the group VIIB metal is At.

23. The metal complex of claim 18, wherein the metal atom is Ag.

24. The metal complex of claim 18, wherein the metal atom is Gd.

25. The metal complex of claim 14, wherein said N-heterocylic carbene substituted porphyrin has the following general formula:

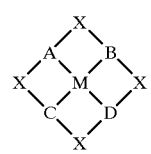

wherein A-D may be the same or different and may be selected from one of the following formulas, with the proviso that at least one of A-D is N-heterocyclic carbene:

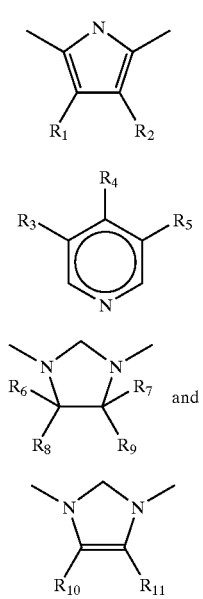

wherein $R_1$–$R_{11}$ may be hydrogen and organic groups including alkyl, cyclo alkyl, substituted cycloalkyl, alkenyl, cycloalkenyl, substituted cycloalkenyl, alkynyl, aryl, substituted aryl, arylalkyl, alkylaryl, and alkoxy;

wherein x may be $CR_{12}$ or $CR_{13}R_{14}$, where $R_{12}$, $R_{13}$ and $R_{14}$ may be hydrogen and organic groups including alkyl, cyclo alkyl, substituted cycloalkyl, alkenyl, cycloalkenyl, substitute cycloalkenyl, alkynyl, aryl, substituted aryl, arylalkyl, alkylaryl, and alkoxy; and wherein M is a metal.

26. The composition of matter of claim 25, wherein each of $R_1$–$R_{14}$ contains from 1 carbon atom to about 10 carbon atoms.

27. The composition of claim 26, wherein each of $R_1$–$R_{14}$ contains from 1 carbon atom to about 6 carbon atoms.

28. The metal complex of claim 25, wherein said metal atom is selected from the group consisting of IIA metals, group IIA metals, group IIIA metals, group IVA metals, group VA metals, group VIA metals, group VIIA metals, and group VIIIA metals, group IVB metals, group VB metals, group VIB metals, VIIB metals, lanthanides and actinides.

29. The metal complex of claim 28, wherein the group IVB metals are selected from the group consisting of Si, Ge, SN and Pb.

30. The metal complex of claim 28, wherein the group VIB metals are selected from the group consisting of Te and Po.

31. The metal complex of claim 28, wherein the group VB metals are selected from the group consisting of P, As, Sb and Bi.

32. The metal complex of claim 28, wherein the group VIIB metal is At.

33. The metal complex of claim 28, wherein the metal atom is Ag.

34. The metal complex of claim 28, wherein the metal atom is Gd.

35. The metal complex of claim 14, wherein the N-heterocylic carbene substituted porphyrin is represented by the following formula:

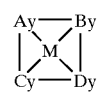

wherein A-D may be the same or different and may be selected from one of the following formulas, with the proviso that at least one of A-D is N-heterocyclic carbene:

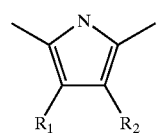

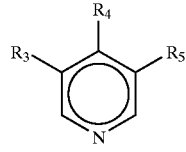

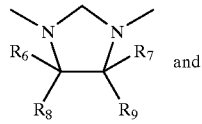

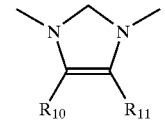

wherein $R_1$–$R_{11}$ may be hydrogen and organic groups including alkyl, cyclo alkyl, substituted cycloalkyl, alkenyl, cycloalkenyl, substituted cycloalkenyl, alkynyl, aryl, substituted aryl, arylalkyl, alkylaryl, and alkoxy, wherein Ay, By, Cy and Dy is 1 or greater with the proviso that at least one of Ay, By, Cy and Dy is at least 2; and wherein M is a metal.

36. The metal complex of claim 35, wherein each of $R_1$–$R_{11}$ contains from 1 carbon atom to about 10 carbon atoms.

37. The metal complex of claim 36, wherein each of $R_1$–$R_{11}$ contains from 1 carbon atom to about 6 carbon atoms.

38. The metal complex of claim 35, wherein said metal atom is selected from the group consisting of IIA metals, group IIA metals, group IIIA metals, group IVA metals, group VA metals, group VIA metals, group VIIA metals, and group VIIIA metals, group IVB metals, group VB metals, group VIB metals, VIIB metals, lanthanides and actinides.

39. The metal complex of claim 35, wherein the group IVB metals are selected from the group consisting of Si, Ge, SN and Pb.

40. The metal complex of claim 35, wherein the group VIB metals are selected from the group consisting of Te and Po.

41. The metal complex of claim 35, wherein the group VB metals are selected from the group consisting of P, As, Sb and Bi.

42. The metal complex of claim 35, wherein the group VIIB metal is At.

43. The metal complex of claim 35, wherein the metal atom is Ag.

44. The metal complex of claim 35, wherein the metal atom is Gd.

45. The metal complex of claim 14, wherein the N-heterocylic carbene substituted porphyrin is represented by the following formula:

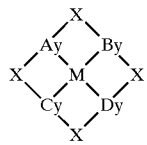

wherein A-D may be the same or different and may be selected from one of the following formulas, with the proviso that at least one of A-D is N-heterocyclic carbene:

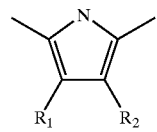
(VIII)

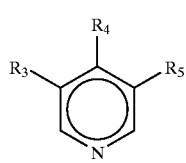
(IX)

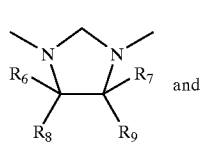
(Xa)
and

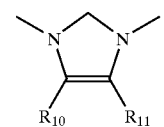
(Xb)

wherein $R_1$–$R_{11}$ may be hydrogen and organic groups including alkyl, cyclo alkyl, substituted cycloalkyl, alkenyl, cycloalkenyl, substituted cycloalkenyl, alkynyl, aryl, substituted aryl, arylalkyl, alkylaryl, and alkoxy, wherein Ay, By, Cy and Dy is 1 or greater with the proviso that at least one of Ay, By, Cy and Dy is at least 2;

wherein x may be $CR_{12}$ or $CR_{13}R_{14}$, where $R_{12}$, $R_{13}$ and $R_{14}$ may be hydrogen and organic groups including alkyl, cyclo alkyl, substituted cycloalkyl, alkenyl, cycloalkenyl, substitute cycloalkenyl, alkynyl, aryl, substituted aryl, arylalkyl, alkylaryl, and alkoxy; and wherein M is a metal.

46. The metal complex of claim 45, wherein each of $R_1$–$R_{14}$ contains from 1 carbon atom to about 10 carbon atoms.

47. The metal complex of claim 45, wherein each of $R_1$–$R_{14}$ contains from 1 carbon atom to about 6 carbon atoms.

48. The metal complex of claim 45, wherein said metal atom is selected from the group consisting of IIA metals, group IIA metals, group IIIA metals, group IVA metals, group VA metals, group VIA metals, group VIIA metals, and group VIIIA metals, group IVB metals, group VB metals, group VIB metals, VIIB metals, lanthanides and actinides.

49. The metal complex of claim 46, wherein the group IVB metals are selected from the group consisting of Si, Ge, SN and Pb.

50. The metal complex of claim 46, wherein the group VIB metals are selected from the group consisting of Te and Po.

51. The metal complex of claim 46, wherein the group VB metals are selected from the group consisting of P, As, Sb and Bi.

52. The metal complex of claim 46, wherein the group VIIB metal is At.

53. The metal complex of claim 46, wherein the metal atom is Ag.

54. The metal complex of claim 46, wherein the metal atom is Gd.

55. A composition of matter comprising:
  a N-heterocylic carbene substituted porphyrin;
  at least one metal atom bonded to said N-heterocylic carbene substituted porphyrin; and
  a targeting moiety bonded to said N-heterocylic carbene substituted porphyrin.

56. The composition of matter of claim 55, wherein said N-heterocylic carbene substituted porphyrin has the following general formula:

(VI)

wherein A-D may be the same or different and may be selected from one of the following formulas, with the proviso that at least one of A-D is N-heterocyclic carbene:

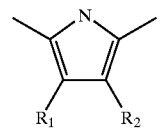
(VIII)

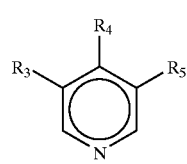
(IX)

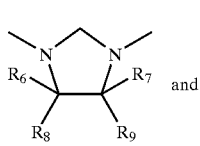
(Xa)
and

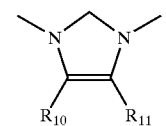
(Xb)

wherein $R_1$–$R_{11}$ may be hydrogen and organic groups including alkyl, cyclo alkyl, substituted cycloalkyl, alkenyl, cycloalkenyl, substituted cycloalkenyl, alkynyl, aryl, substituted aryl, arylalkyl, alkylaryl, and alkoxy.

57. The composition of matter of claim 56, wherein each of $R_1$–$R_{11}$ contains from 1 carbon atom to about 10 carbon atoms.

58. The composition of matter of claim 57, wherein each of $R_1$–$R_{11}$ contains from 1 carbon atom to about 6 carbon atoms.

59. The composition of matter of claim 56, wherein said metal atom is selected from the group consisting of IIA metals, group IIA metals, group IIIA metals, group IVA metals, group VA metals, group VIA metals, group VIIA metals, and group VIIIA metals, group IVB metals, group VB metals, group VIB metals, VIIB metals, lanthanides and actinides.

60. The composition of matter of claim 59, wherein the group IVB metals are selected from the group consisting of Si, Ge, SN and Pb.

61. The composition of matter of claim 59, wherein the group VIB metals are selected from the group consisting of Te and Po.

62. The composition of matter of claim 59, wherein the group VB metals are selected from the group consisting of P, As, Sb and Bi.

63. The composition of matter of claim 59, wherein the group VIIB metal is At.

64. The composition of matter of claim 59, wherein the metal atom is Ag.

65. The composition of matter of claim 59, wherein the metal atom is Gd.

66. The composition of matter of claim 55, wherein said N-heterocylic carbene substituted porphyrin has the following general formula:

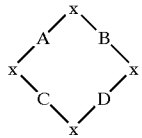

(VII)

wherein A-D may be the same or different and may be selected from one of the following formulas, with the proviso that at least one of A-D is N-heterocyclic carbene:

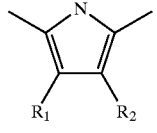

(VIII)

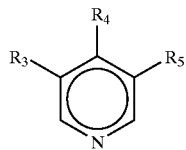

(IX)

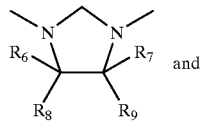

(Xa)

and

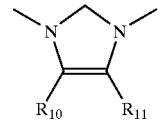

(Xb)

wherein $R_1$–$R_{11}$ may be hydrogen and organic groups including alkyl, cyclo alkyl, substituted cycloalkyl, alkenyl, cycloalkenyl, substituted cycloalkenyl, alkynyl, aryl, substituted aryl, arylalkyl, alkylaryl, and alkoxy; and wherein x may be $CR_{12}$ or $CR_{13}R_{14}$, where $R_{12}$, $R_{13}$ and $R_{14}$ may be hydrogen and organic groups including alkyl, cyclo alkyl, substituted cycloalkyl, alkenyl, cycloalkenyl, substitute cycloalkenyl, alkynyl, aryl, substituted aryl, arylalkyl, alkylaryl, and alkoxy.

67. The composition of matter of claim 66, wherein each of $R_1$–$R_{14}$ contains from 1 carbon atom to about 10 carbon atoms.

68. The composition of matter of claim 67, wherein each of $R_1$–$R_{14}$ contains from 1 carbon atom to about 6 carbon atoms.

69. The composition of matter of claim 66, wherein said metal atom is selected from the group consisting of IIA metals, group IIA metals, group IIIA metals, group IVA metals, group VA metals, group VIA metals, group VIIA metals, and group VIIIA metals, group IVB metals, group VB metals, group VIB metals, VIIB metals, lanthanides and actinides.

70. The composition of matter of claim 69, wherein the group IVB metals are selected from the group consisting of Si, Ge, SN and Pb.

71. The composition of matter of claim 69, wherein the group VIB metals are selected from the group consisting of Te and Po.

72. The composition of matter of claim 69, wherein the group VB metals are selected from the group consisting of P, As, Sb and Bi.

73. The composition of matter of claim 69, wherein the group VIIB metal is At.

74. The composition of matter of claim 69, wherein the metal atom is Ag.

75. The composition of matter of claim 69, wherein the metal atom is Gd.

76. The composition of matter of claim 55, wherein the N-heterocylic carbene substituted porphyrin is represented by the following formula:

(XI)

wherein A-D may be the same or different and may be selected from one of the following formulas, with the proviso that at least one of A-D is N-heterocyclic carbene:

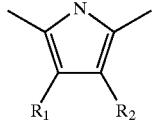

(VIII)

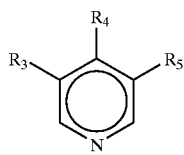

(IX)

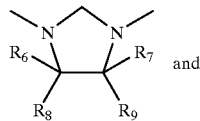 (Xa)

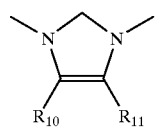 (Xb)

wherein $R_1$–$R_{11}$ may be hydrogen and organic groups including alkyl, cyclo alkyl, substituted cycloalkyl, alkenyl, cycloalkenyl, substituted cycloalkenyl, alkynyl, aryl, substituted aryl, arylalkyl, alkylaryl, and alkoxy, wherein Ay, By, Cy and Dy is 1 or greater with the proviso that at least one of Ay, By, Cy and Dy is at least 2.

77. The composition of matter of claim 76, wherein each of $R_1$–$R_{11}$ contains from 1 carbon atom to about 10 carbon atoms.

78. The composition of matter of claim 77, wherein each of $R_1$–$R_{11}$ contains from 1 carbon atom to about 6 carbon atoms.

79. The composition of matter of claim 76, wherein said metal atom is selected from the group consisting of IIA metals, group IIA metals, group IIIA metals, group IVA metals, group VA metals, group VIA metals, group VIIA metals, and group VIIIA metals, group IVB metals, group VB metals, group VIB metals, VIIB metals, lanthanides and actinides.

80. The composition of matter of claim 79, wherein the group IVB metals are selected from the group consisting of Si, Ge, SN and Pb.

81. The composition of matter of claim 79, wherein the group VIB metals are selected from the group consisting of Te and Po.

82. The composition of matter of claim 79, wherein the group VB metals are selected from the group consisting of P, As, Sb and Bi.

83. The composition of matter of claim 79, wherein the group VIIB metal is At.

84. The composition of matter of claim 79, wherein the metal atom is Ag.

85. The composition of matter of claim 79, wherein the metal atom is Gd.

86. The composition of matter of claim 55, wherein the N-heterocylic carbene substituted porphyrin is represented by the following formula:

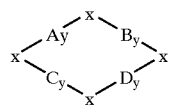 (XII)

wherein A-D may be the same or different and may be selected from one of the following formulas, with the proviso that at least one of A-D is N-heterocyclic carbene:

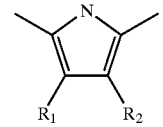 (VIII)

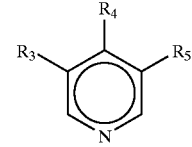 (IX)

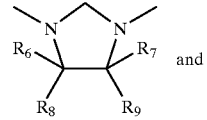 (Xa)

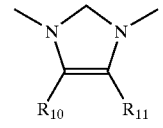 (Xb)

wherein $R_1$–$R_{11}$ may be hydrogen and organic groups including alkyl, cyclo alkyl, substituted cycloalkyl, alkenyl, cycloalkenyl, substituted cycloalkenyl, alkynyl, aryl, substituted aryl, arylalkyl, alkylaryl, and alkoxy, wherein Ay, By, Cy and Dy is 1 or greater with the proviso that at least one of Ay, By, Cy and Dy is at least 2; and wherein x may be $CR_{12}$ or $CR_{13}R_{14}$, where $R_{12}$, $R_{13}$ and $R_{14}$ may be hydrogen and organic groups including alkyl, cyclo alkyl, substituted cycloalkyl, alkenyl, cycloalkenyl, substitute cycloalkenyl, alkynyl, aryl, substituted aryl, arylalkyl, alkylaryl, and alkoxy.

87. The composition of matter of claim 86, wherein each of $R_1$–$R_{14}$ contains from 1 carbon atom to about 10 carbon atoms.

88. The composition of matter of claim 87, wherein each of $R_1$–$R_{14}$ contains from 1 carbon atom to about 6 carbon atoms.

89. The composition of matter of claim 86, wherein said metal atom is selected from the group consisting of IIA metals, group IIA metals, group IIIA metals, group IVA metals, group VA metals, group VIA metals, group VIIA metals, and group VIIIA metals, group IVB metals, group VB metals, group VIB metals, VIIB metals, lanthanides and actinides.

90. The composition of matter of claim 89, wherein the group IVB metals are selected from the group consisting of Si, Ge, SN and Pb.

91. The composition of matter of claim 89, wherein the group VIB metals are selected from the group consisting of Te and Po.

92. The composition of matter of claim 89, wherein the group VB metals are selected from the group consisting of P, As, Sb and Bi.

93. The composition of matter of claim 89, wherein the group VIIB metal is At.

94. The composition of matter of claim 89, wherein the metal atom is Ag.

95. The composition of matter of claim 89, wherein the metal atom is Gd.

96. The composition of claim 55, wherein the targeting moiety is selected form the group consisting of biotin and nitroimidazoles.

97. The composition of claim 55, wherein said linker is selected from the group consisting of alkyl, substituted alkyl, alkenyl, substituted alkenyl, alkynyl, substituted alkynyl, aryl, substituted aryl, arylalkyl, alkylaryl, alkoxy, amines, amides, and polyethers.

* * * * *